United States Patent
Yoon et al.

(10) Patent No.: US 10,251,623 B2
(45) Date of Patent: Apr. 9, 2019

(54) SUPPORT APPARATUS OF ULTRASOUND PROBE, HANDSFREE ULTRASOUND PROBE INCLUDING THE SUPPORT APPARATUS, AND METHOD OF OPERATING THE SUPPORT APPARATUS

(71) Applicant: SAMSUNG MEDISON CO., LTD., Gangwon-Do (KR)

(72) Inventors: Jeong-un Yoon, Gangwon-do (KR); Jae-Moon Jo, Gangwon-do (KR); Jong-Sik Kim, Gangwon-do (KR); Gil-Ju Jin, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 693 days.

(21) Appl. No.: 14/535,173

(22) Filed: Nov. 6, 2014

(65) Prior Publication Data

US 2015/0126871 A1 May 7, 2015

(30) Foreign Application Priority Data

Nov. 6, 2013 (KR) .......................... 10-2013-0134355

(51) Int. Cl.
*A61B 8/00* (2006.01)

(52) U.S. Cl.
CPC .......... *A61B 8/4209* (2013.01); *A61B 8/4236* (2013.01); *A61B 8/4444* (2013.01);
(Continued)

(58) Field of Classification Search
CPC ... A61B 8/4209; A61B 8/4236; A61B 8/4444; A61B 8/467; A61B 8/54
See application file for complete search history.

(56) References Cited

U.S. PATENT DOCUMENTS 7,322,116 B2 * 1/2008 Long .................... G01C 15/002
248/205.5
2004/0087851 A1 5/2004 Lee
(Continued)

FOREIGN PATENT DOCUMENTS

CN 201211198 Y 3/2009
CN 102824191 A 12/2012
(Continued)

OTHER PUBLICATIONS

English translation of JP 2008-061894 A, provided by Japan Platform for Patent Information.*
(Continued)

*Primary Examiner* — Thomas J Hong
*Assistant Examiner* — Colin T. Sakamoto
(74) *Attorney, Agent, or Firm* — Morgan Lewis & Bockius LLP (57) ABSTRACT

A support apparatus of an ultrasound probe, a handsfree ultrasound probe including the support apparatus, and a method of operating the support apparatus. The support apparatus includes: a housing including an accommodation unit capable of accommodating an ultrasound probe and an adhesion unit capable of contacting a target object; and a first control unit for controlling an adhesive force with respect to the target object of the adhesion unit according to whether a user touches at least one of the ultrasound probe and the housing.

7 Claims, 9 Drawing Sheets

(52) U.S. Cl.
CPC ............... *A61B 8/467* (2013.01); *A61B 8/54* (2013.01); *A61B 8/4427* (2013.01)

(56) References Cited

U.S. PATENT DOCUMENTS

2010/0174189 A1 7/2010 Abraham
2012/0296216 A1 11/2012 Sharf et al.

FOREIGN PATENT DOCUMENTS

| JP | 2006230913 A | 9/2006 |
|---|---|---|
| JP | 2008-061894 A | 3/2008 |

OTHER PUBLICATIONS

European Communication pursuant to Article 94(3) EPC, issued in corresponding European Patent Application No. 14157985.4, dated May 20, 2016.
Extended European Search Report issued in Application No. 14157985.4 dated Aug. 5, 2014.
Chinese Office Action dated Sep. 30, 2018 issued in Chinese Patent Application No. 201410407963.3 (with English translation).

* cited by examiner

SUPPORT APPARATUS OF ULTRASOUND PROBE, HANDSFREE ULTRASOUND PROBE INCLUDING THE SUPPORT APPARATUS, AND METHOD OF OPERATING THE SUPPORT APPARATUS

RELATED APPLICATIONS

This application claims the benefit of Korean Patent Application No. 10-2013-0134355, filed on Nov. 6, 2013, in the Korean Intellectual Property Office, the disclosure of which is incorporated herein in its entirety by reference.

BACKGROUND

1. Field

One or more embodiments of the present invention relate to a support apparatus of an ultrasound probe, a handsfree ultrasound probe including the support apparatus, and a method of operating the support apparatus.

2. Description of the Related Art

An ultrasound apparatus, a magnetic resonance imaging (MRI) apparatus, a computed tomography (CT) apparatus, an X-ray apparatus, etc. may be used as medical devices for obtaining a medical image of a body. By reason of a resolution of the medical image or a size of the medical device, these apparatuses may photograph a part of the body or an overall part of the body. The overall part of the body may be photographed at a time or the part of the body may be photographed in several times and then photographed images may be combined into one image to obtain a combined image of the whole part of the body.

An ultrasound diagnosis apparatus includes an ultrasound probe that transmits and receives ultrasound, a signal processing apparatus that performs signal processing on the received ultrasound, and a display apparatus that displays an ultrasound image.

The ultrasound probe that a user who is a doctor is holding by his/her hand contacts a target object such as a patient body, transmits ultrasound to the target object, and receives an echo signal of the ultrasound. However, although a user needs to fix the ultrasound probe to the target object when more closely diagnosing a specific part of the target object, it is difficult to fix the ultrasound probe more than a predetermined period of time due to a weight of the ultrasound probe.

SUMMARY

One or more embodiments of the present invention include a support apparatus of an ultrasound probe that a user may not hold by his/her hand during a diagnosis, a handsfree ultrasound probe including the support apparatus, and a method of operating the support apparatus.

One or more embodiments of the present invention include a support apparatus of an ultrasound probe capable of remotely controlling a movement of the ultrasound probe, a handsfree ultrasound probe including the support apparatus, and a method of operating the support apparatus.

Additional aspects will be set forth in part in the description which follows and, in part, will be apparent from the description, or may be learned by practice of the presented embodiments.

According to one or more embodiments of the present invention, a support apparatus of an ultrasound acoustic probe, the support apparatus including: a housing including an accommodation unit capable of accommodating an ultrasound probe and an adhesion unit capable of contacting a target object; and a first control unit for controlling an adhesive force with respect to the target object of the adhesion unit according to whether a user touches at least one of the ultrasound probe and the housing.

The adhesive force when a user touch is detected may be smaller than that when the user touch is not detected.

The first control unit may control the adhesive force to be smaller than a first reference value if a user touch is detected, and control the adhesive force to be greater than the first reference value if the user touch is not detected.

The first control unit may be capable of adjusting an intensity of the adhesive force at steps.

The first control unit may control the adhesive force by using an amount of air between the adhesion unit and the target object.

The first control unit may include a vacuum pump that adjusts the amount of air.

The support apparatus may further include: a second control unit for controlling a movement of the ultrasound probe according to whether the user touches at least one of the ultrasound probe and the housing.

The second control unit may include an actuator that is capable of moving such that the actuator contacts the ultrasound probe or is spaced apart from the ultrasound probe.

The actuator may be spaced apart from the ultrasound probe such that the ultrasound probe moves if the user touch is detected, and fix the ultrasound probe if the user touch is not detected.

The actuator may move the ultrasound probe in correspondence to a user command used to move the ultrasound probe if the user touch is not detected, and the user command is input.

The actuator may move at a trace of a protocol that is previously stored in correspondence to the user command.

The user command may be remotely input.

The first control unit may receive whether the user touches at least one of the ultrasound probe and the housing from a sensor disposed in at least one of the ultrasound probe and the housing.

The sensor may include at least one of a touch sensor, a temperature sensor, a button sensor, a light sensor, and a pressure sensor.

The ultrasound probe may be detached from the accommodation unit.

According to one or more embodiments of the present invention, a handsfree ultrasound probe including: an ultrasound probe for irradiating ultrasound to a target object and receiving an echo signal of the ultrasound; an accommodation unit for accommodating the ultrasound probe; and an adhesion unit for contacting the target object.

The handsfree ultrasound probe may further include: a first control unit for controlling an adhesive force with respect to the target object of the adhesion unit according to whether a user touches the handsfree ultrasound probe.

The first control unit may control the adhesive force when a user touch is not detected to be greater smaller than that when the user touch is detected.

According to one or more embodiments of the present invention, a method of operating a handsfree ultrasound probe, the method including: detecting whether a user touches the handsfree ultrasound probe; and controlling an adhesive force of the handsfree ultrasound probe with respect to a target object to be smaller than a first reference value if it is detected that the user touches the handsfree ultrasound probe.

The method may further include: controlling the adhesive force of the handsfree ultrasound probe with respect to the target object to be greater than the first reference value if it is not detected that the user touches the handsfree ultrasound probe.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout, and redundant explanations are omitted. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Throughout the specification, a term 'target object' may include a person, animal, or a part of a person or animal. For example, the target object may include organs such as the liver, the heart, the womb, the brain, the breast, the abdominal region, etc., or a blood vessel. Throughout the specification, a "user" may be a medical expert including a doctor, a nurse, a medical laboratory technologist, a medical image expert, a technician repairing medical equipments, or the like.

Figure 1:
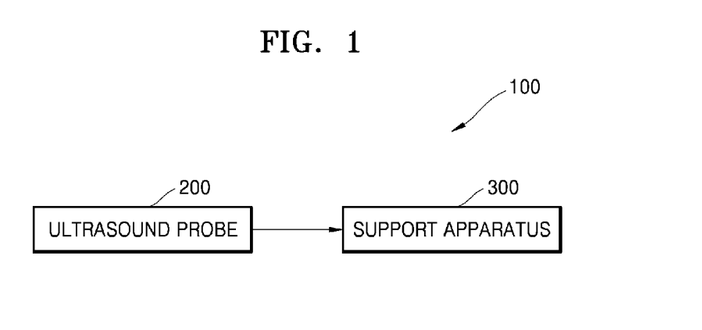
FIG. 1 is a schematic block diagram of a handsfree ultrasound probe according to an embodiment of the present invention.
Figure 2:
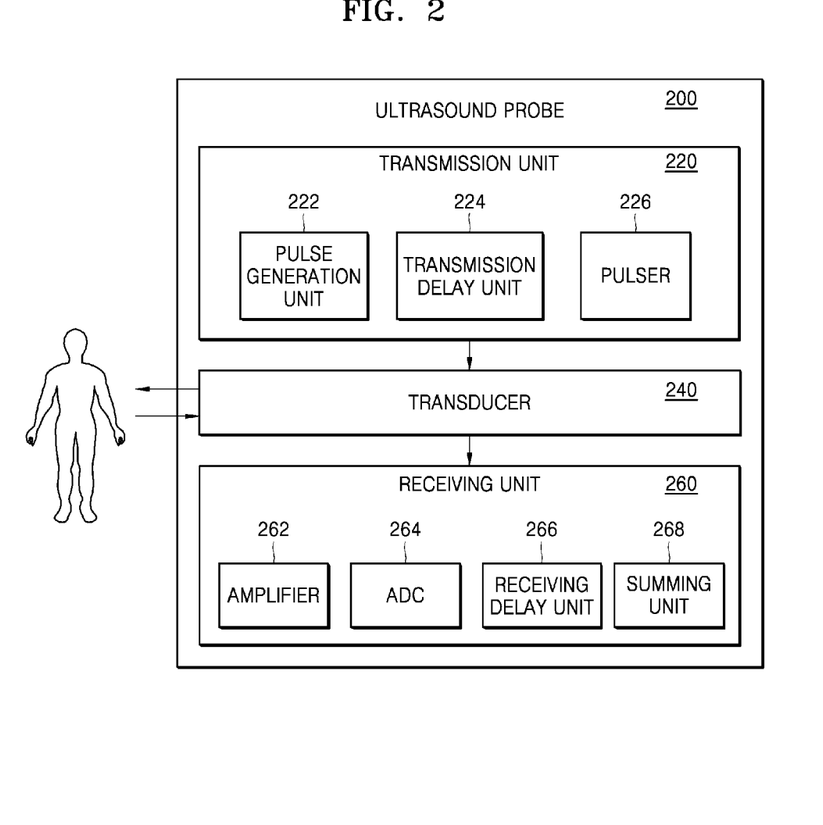
FIG. 2 is a block diagram of an ultrasound probe shown in FIG. 1.
Figure 3:
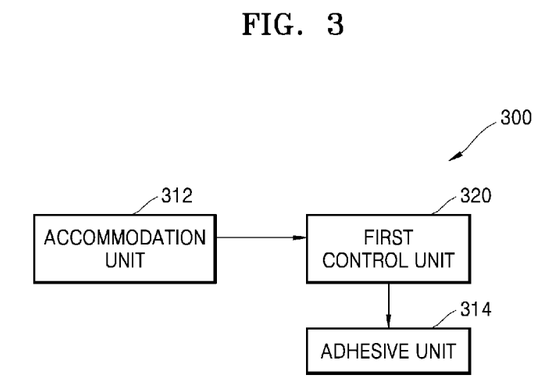
FIG. 3 is a block diagram of a support apparatus shown in FIG. 1.
Figure 4A:
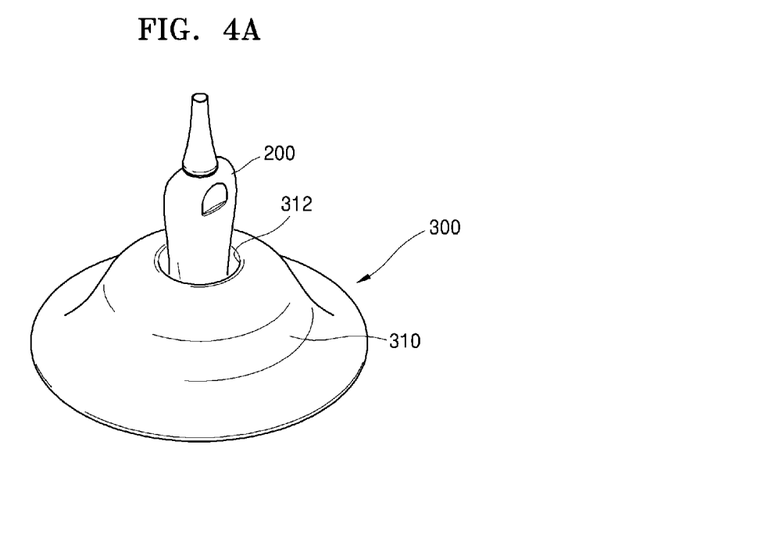
FIG. 4A illustrates an external appearance of the support apparatus shown in FIG. 1.
Figure 4B:
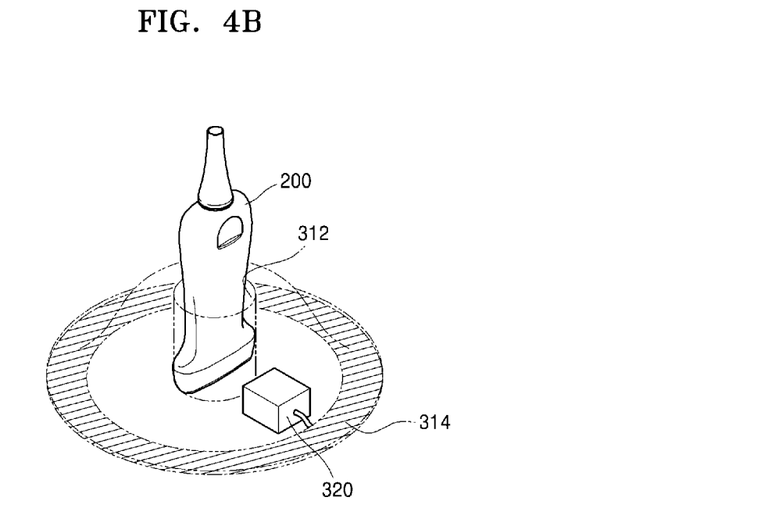
FIG. 4B illustrates an internal appearance of the support apparatus shown in FIG. 1.

FIG. 1 is a schematic block diagram of a handsfree ultrasound probe 100 according to an embodiment of the present invention. FIG. 2 is a block diagram of an ultrasound probe 200 shown in FIG. 1. FIG. 3 is a block diagram of a support apparatus 300 shown in FIG. 1. FIG. 4A illustrates an external appearance of the support apparatus 300 shown in FIG. 1. FIG. 4B illustrates an internal appearance of the support apparatus 300 shown in FIG. 1.

Referring to FIG. 1, the handsfree ultrasound probe 100 includes the ultrasound probe 200 that photographs a target objet by using ultrasound to generate an ultrasound image and the support apparatus 300 that supports the ultrasound probe 200 to contact the target object.

The ultrasound probe 200 transmits ultrasound to the target object and receives an echo signal of the ultrasound from the target object. The ultrasound probe 200 may include a transmission unit 220, a transducer 240, and a receiving unit 260 as shown in FIG. 2.

The transmission unit 220 provides the transducer 240 with a driving signal. The transmission unit 220 may include a pulse generation unit 222, a transmission delay unit 224, and a pulser 226.

The pulse generation unit 222 generates rate pulses for forming transmission ultrasound according to a predetermined pulse repetition frequency (PRF). The transmission delay unit 224 applies delay time to the rate pulses generated by the pulse generation unit 222 to determine a transmission directionality. The rate pulses to which the delay time is applied respectively correspond to a plurality of unit devices included in the transducer 240. The pulser 226 applies the driving signal (or a driving pulse) to the transducer 240 at timing corresponding to each of the rate pulses to which the delay time is applied. The unit devices may be in a one-dimensional array or a two-dimensional array.

The transducer 240 sends the ultrasound to the target object according to the driving signal provided by the transmission unit 220 and receives the echo signal of the ultrasound reflected from the target object. The transducer 240 may include a plurality of unit devices that convert an electrical signal into acoustic energy (or vice versa). The unit devices may be in a one-dimensional array or a two-dimensional array.

The transducer 240 may be implemented as a piezoelectric micromachined ultrasonic (pMUT) that inter-converts the ultrasound and the electrical signal by using a change in pressure while vibrating, a capacitive MUT (cMUT) that inter-converts the ultrasound and the electrical signal by using a change in capacitance, a magnetic MUT (mMUT) that inter-converts the ultrasound and the electrical signal by using a change in a magnetic field, an optical ultrasound detector that inter-converts the ultrasound and the electrical signal by using a change in an optical characteristic, etc.

The receiving unit 260 may generate ultrasound data by processing signals received from the transducer 240, and include an amplifier 262, an analogue digital converter (ADC) 264, a receiving delay unit 266, and a summing unit 268.

The amplifier 262 amplifies the signals received from the transducer 240. The ADC 264 AD-converts the amplified signals. The receiving delay unit 266 applies a delay time used to determine a reception directionality to the digitally converted signals. The summing unit 268 generates the ultrasound data by summing signals processed by the receiving delay unit 266. A reflective component may be emphasized from a direction determined by the reception directionality according to the summing performed by the summing unit 268.

Although the ultrasound probe 200 necessarily includes the transducer 240, some elements of the transmission unit 220 and the receiving unit 260 may be included in another apparatus. For example, the ultrasound probe 200 may not include the summing unit 268 of the receiving unit 260.

The support apparatus 300 may include a housing 310 that forms an external appearance thereof and a first control unit 320 that controls an adhesive force with respect to a target object of the housing 310 according to whether the user touches at least one of the ultrasound probe 200 and the housing 310.

The housing 310 may include an accommodation unit 312 that is capable of accommodating the ultrasound probe 200 and an adhesion unit 314 that is capable of being adhered to the target object. The ultrasound probe 200 may be detachable from the accommodation unit 312. The accommodation unit 312 may be formed as a hole that passes through the housing 310 so that the ultrasound probe 200 may contact the target object but is not limited thereto. The accommodation unit 312 may be a groove formed inside the housing 310 or may be a space between a coverer 316 and the adhesion unit 314 of the housing 310.

The adhesion unit 314 may be a floor surface of the housing 310 to contact the target object. When the accommodation unit 312 is formed as the hole or the groove, the adhesion unit 314 may be disposed to surround the accommodation unit 312. When the accommodation unit 312 is a space inside the housing 310, the adhesion unit 314 may be the whole floor surface of the housing 310. The adhesion unit 314 may be formed of an elastic material. A shape of the adhesion unit 314 may be slightly changed according to an adhesive force with respect to the target object.

The first control unit 320 controls the adhesive force with respect to the target object of the adhesion unit 314 according to whether the user touches at least one of the ultrasound probe 200 and the housing 310. For example, if it is detected that the user touches at least one of the ultrasound probe 200 and the housing 310, the first control unit 320 controls the adhesive force to be smaller than a first reference value, and, if it is not detected that the user touches at least one of the ultrasound probe 200 and the housing 310, the first control unit 320 controls the adhesive force to be greater than the first reference value. That is, the adhesive force with respect to the target object when a user touch is detected is smaller than that when the user touch is not detected. When the user touches the ultrasound probe 200 or the housing 310, since the adhesive force with respect to the target object is weak, the handsfree ultrasound probe 100 may freely move. When the user does not touch the ultrasound probe 200 or the housing 310, since the adhesive force with respect to the target object is strong, the handsfree ultrasound probe 100 may contact the target object.

The first control unit 30 may control an intensity of the adhesive force by using an amount of air between the adhesion unit 314 and the target object. For example, the first control unit 320 may include a vacuum pump capable of adjusting the amount of air. That is, the first control unit 320 may control the adhesive force to be stronger by reducing the amount of air between the adhesion unit 314 and the target object and may control the adhesive force to be weaker by increasing the amount of air between the adhesion unit 314 and the target object. The first control unit 320 may be disposed inside the housing 310 but is not limited thereto. The first control unit 320 may be disposed on the cover 316.

In addition, the first control unit 320 may adjust the intensity of the adhesive force at plural steps. For example, if the user touch is not detected, the first control unit 320 controls the adhesive force to be greater than the first reference value, and, if the user touch is detected, when an angle movement of the ultrasound probe 200 is detected, the first control unit 320 controls the adhesive force to be smaller than the first reference value and to be greater than a second reference value. When the user touch is detected, if a rectilinear movement (for example, a movement in a normal line direction or a tangent line direction with respect to the target object) of the ultrasound probe 200 is detected, the first control unit 320 controls the adhesive force to be smaller than the second reference value. The first control unit 320 may include elements in addition to the vacuum pump. For example, the first control unit 320 may be a motor that applies a pressure to contact the adhesion unit 314 to the target object or that separates the adhesion unit 314 from the target object.

Since the adhesive force with respect to the target object differs according to whether there is the user touch as described above, the user does not need to place the handsfree ultrasound probe 100 in a specific portion of the target object and hold the handsfree ultrasound probe 100. Thus, a pain in an arm that is like to occur by operating the ultrasound probe 200 may be reduced. The user may operate another function of an ultrasound diagnosis apparatus without using his/her hand to fix the ultrasound probe 200, thereby conveniently operating the ultrasound diagnosis apparatus. Furthermore, the handsfree ultrasound probe 100 may photograph an image with respect to a specific region of the target object for a predetermined period of time without shaking, and thus the user may accurately diagnose the specific region.

Figure 5:
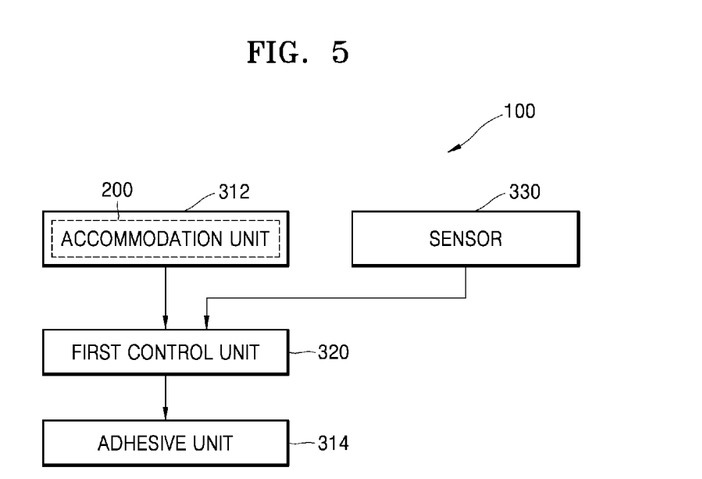
FIG. 5 is a schematic block diagram of a handsfree ultrasound probe according to another embodiment of the present invention.

FIG. 5 is a schematic block diagram of the handsfree ultrasound probe 100 according to another embodiment of the present invention. Referring to FIG. 5, the handsfree ultrasound probe 100 may further include a sensor 330 that detects a user touch with respect to at least one of the ultrasound probe 200 and the housing 310 of the support apparatus 300. The sensor 330 may be at least one of a touch sensor, a temperature sensor, a button sensor, a light sensor, and a pressure sensor. The sensor 330 may be disposed in the ultrasound probe 200 or in the housing 310 of the support apparatus 300. If the sensor 330 is disposed in the ultrasound probe 200, the sensor 330 may be electrically connected to the first control unit 320 when the ultrasound probe 200 is accommodated in the accommodation unit 312 of the support apparatus 300. Thus, a detection result of the sensor 330 may be applied to the first control unit 320.

Figure 6:
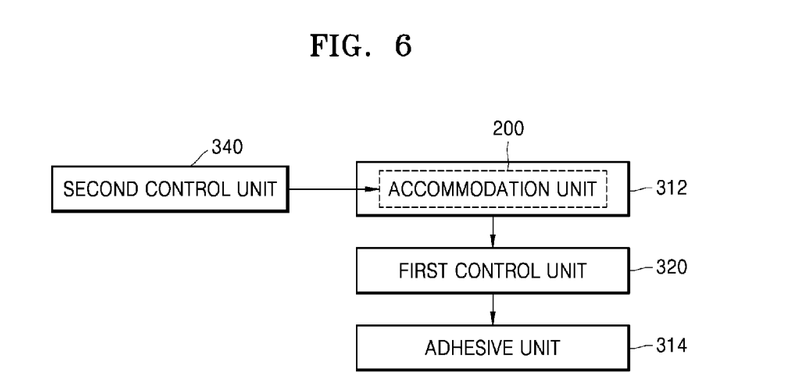
FIG. 6 is a block diagram of a support apparatus of an ultrasound probe according to another embodiment of the present invention.
Figure 7:
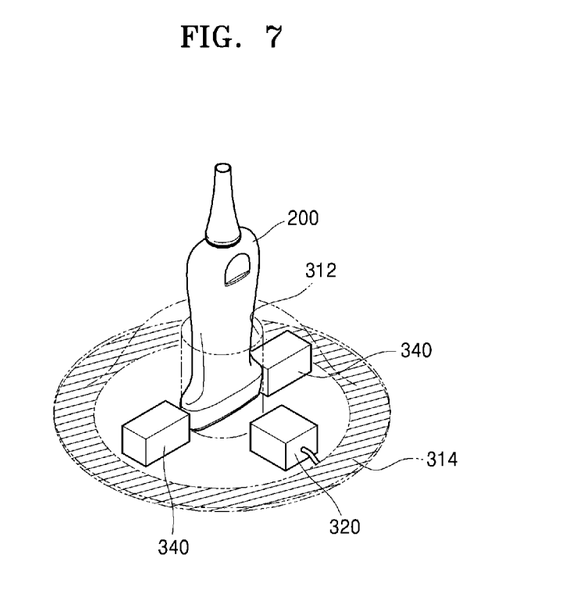
FIG. 7 illustrates an internal appearance of the support apparatus shown in FIG. 6.

FIG. 6 is a block diagram of the support apparatus 300 of the ultrasound probe 200 according to another embodiment of the present invention. FIG. 7 illustrates an internal appearance of the support apparatus 300 shown in FIG. 6. Compared to the support apparatus 300 shown in FIG. 3, the support apparatus 300 shown in FIG. 6 may further include a second control unit 340 that controls a movement of the ultrasound probe 200 according to whether a user touch is detected. The second control unit 340 may include an actuator that is capable of moving such that the actuator may contact the ultrasound probe 200 or may be spaced apart from the ultrasound probe 200. The actuator may be spaced apart from the ultrasound probe 200 such that the ultrasound probe 200 may move if the user touch is detected. The actuator may contact and fix the ultrasound probe 200 if the user touch is not detected.

Figure 8:
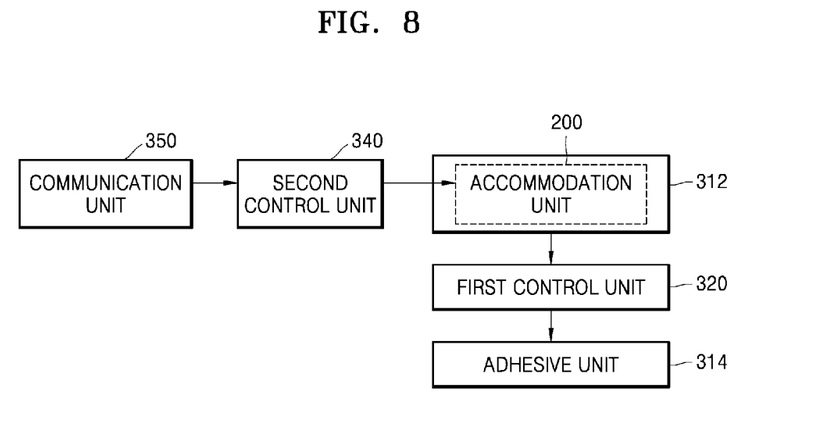
FIG. 8 is a block diagram of a support apparatus of an ultrasound probe according to another embodiment of the present invention.

The second control unit 340 may control a movement of the ultrasound probe 200 according to a protocol that is previous stored. FIG. 8 is a block diagram of the support apparatus 300 of the ultrasound probe 200 according to another embodiment of the present invention. Compared to the support apparatus 300 shown in FIG. 7, the support apparatus 300 shown in FIG. 8 may further include a communication unit 350 that is capable of communicating with an external device. The external device may be a portable terminal as an apparatus capable of inputting a user command. If the ultrasound probe 200 is installed in the accommodation unit 312, the first control unit 320 controls an adhesive force of the adhesion unit 314 to be smaller than a first reference value, and the second control unit 340 fixes the ultrasound probe 200. If a user touch is not detected, the first control unit 320 controls the adhesive force of the adhesion unit 314 to be greater than the first reference value. In addition, if the user touch is not detected, and a user command used to move the ultrasound probe 200 is input through the communication unit 350, the second control unit 340 may move the ultrasound probe 200 according to the user command. The user command may be remotely input. That is, the user command may be input via wireless communication. The second control unit 340 may move the ultrasound probe 200 at one or more degrees of freedom.

Furthermore, if the user command is a movement command according to a protocol that is previous stored. For example, a movement trace of the ultrasound probe 200 may be previously stored according to a type (liver, abdomen, etc.) of a target object that is to be photographed. If a user command used to select the type of the target object is input, the second control unit 340 may move the ultrasound probe 200 to a movement trace corresponding to a selected type of the target object. The communication unit 350 is disposed in the support apparatus 300 in FIG. 7 but is not limited thereto. The communication unit 350 may be disposed in the ultrasound probe 200, and, when the ultrasound probe 200 is accommodated in the accommodation unit 312, may be electrically connected to the second control unit 340.

Figure 9A:
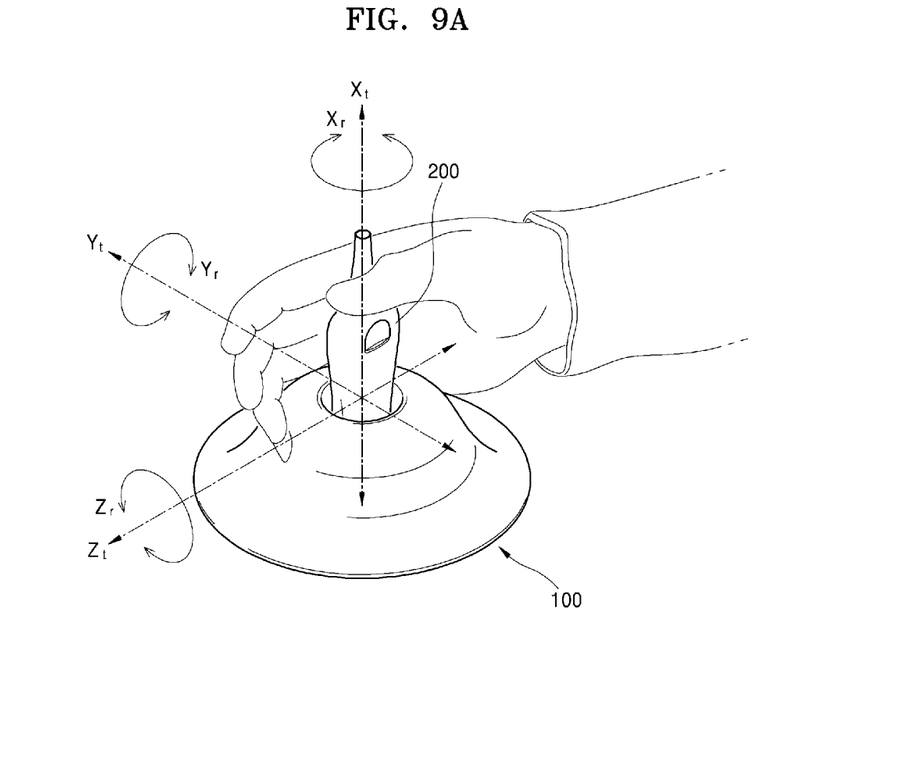
FIGS. 9A through 9C illustrate examples of a user command used to move a handsfree ultrasound probe according to embodiments of the present invention.
Figure 9B:
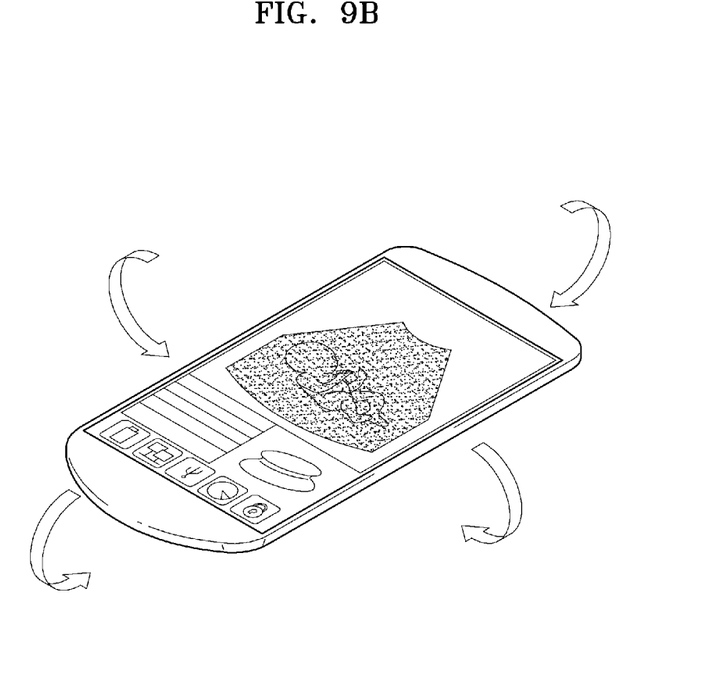
Figure 9C:
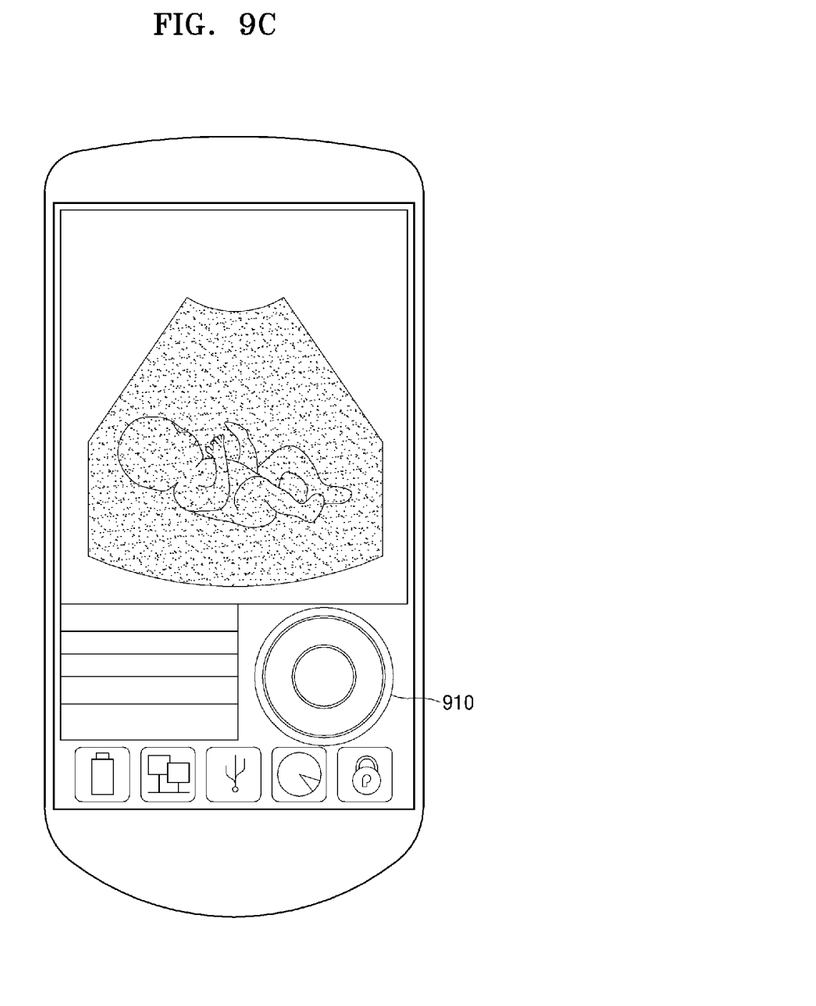

FIGS. 9A through 9C illustrate examples of a user command used to move the handsfree ultrasound probe 100 according to embodiments of the present invention.

Referring to FIG. 9A, after contacting the handsfree ultrasound probe 100 to a target object, a user may move the ultrasound probe 200 at one or more degrees of freedom while holding the ultrasound probe 200.

Alternatively, the user ends touching the handsfree ultrasound probe 100 while contacting the handsfree ultrasound probe 100 to the target object. Referring to FIG. 9B, a user control apparatus, for example, a portable terminal, may be used to control a movement of the ultrasound probe 200. Since a gyro sensor, an acceleration sensor, etc, are embedded in the portable terminal, if the user moves the portable terminal at one or more degrees of freedom, a movement of the portable terminal is transmitted to the handsfree ultrasound probe 100, and the ultrasound probe 200 may move in correspondence to the movement of the portable terminal.

Alternatively, referring to FIG. 9C, an icon 910 used to control a movement of the ultrasound probe 200 may be disposed in the user control apparatus. The user may control the movement of the ultrasound probe 200 by using the icon 910.

Figure 10:
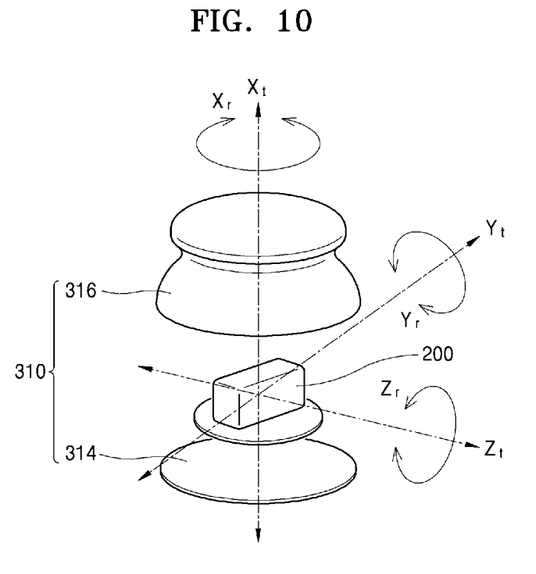
FIG. 10 illustrates an external appearance of a handsfree ultrasound probe according to another embodiment of the present invention.

FIG. 10 illustrates an external appearance of the handsfree ultrasound probe 100 according to another embodiment of the present invention. Referring to FIG. 10, the housing 310 of the support apparatus 300 may be configured as the adhesion unit 314 and the cover 316, and the ultrasound probe 200 may be disposed in an inner space between the adhesion unit 314 and the cover 316. The ultrasound probe 200 may further include a wireless communication unit (not shown) that is capable of communicating with an external device (for example, a signal processing apparatus). Thus, the wireless communication unit may communicate data according to the digital imaging and communication in medicine (DICOM) standard.

Figure 11:
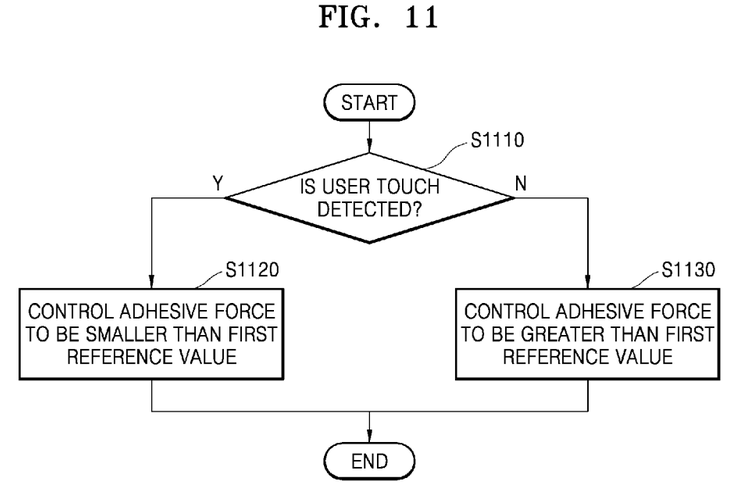
FIG. 11 is a flowchart of a method of operating a handsfree ultrasound probe according to an embodiment of the present invention.

FIG. 11 is a flowchart of a method of operating the handsfree ultrasound probe 100 according to an embodiment of the present invention. Referring to FIG. 11, the sensor 330 detects whether a user touches the handsfree ultrasound probe 100 (operation S1110). The sensor 330 may be disposed in the ultrasound probe 200 or in the support apparatus 300. The sensor 330 may be a touch sensor that is capable of detecting a user touch but is not limited thereto. The sensor 330 may be one of a temperature sensor, a button sensor, a light sensor, and a pressure sensor.

If a user touch is detected (operation S1110—Y), the first control unit 320 may control an adhesive force of the handsfree ultrasound probe 100 with respect to a target object to be smaller than a first reference value (operation S1120). Thus, the user may separate the handsfree ultrasound probe 100 from the target object.

If the user touch is not detected (operation S1110—N), the first control unit 320 may control the adhesive force of the handsfree ultrasound probe 100 with respect to the target object to be greater than the first reference value (operation S1130). Thus, the user may fix the handsfree ultrasound probe 100 to the target object without touching the handsfree ultrasound probe 100 so that the handsfree ultrasound probe 100 may continuously irradiate ultrasound to a specific region of the target object. Alternatively, the user may remotely move the ultrasound probe 200 and photograph an ultrasound image while contacting the ultrasound probe 200 to the target object. For example, if the user touch is not detected, and a user command used to move the ultrasound probe 200 is input, the second control unit 340 may move the ultrasound probe 200 in correspondence to the user command.

As described above, according to the one or more of the above embodiments of the present invention, a user may not hold an ultrasound probe during a diagnosis, thereby increasing a user convenience.

The ultrasound probe moves according to a protocol that is previous stored, thereby more accurately photographing an ultrasound image.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A support apparatus of an ultrasound probe, the support apparatus comprising:
   a housing comprising:
      a space formed inside the housing configured to accommodate an ultrasound probe, and
      a contact surface configured to contact a target object;
   a sensor disposed in at least one of the ultrasound probe and the housing, wherein the sensor is configured to detect whether a user touches said at least one of the ultrasound probe and the housing;

a vacuum pump disposed inside the housing, wherein the vacuum pump is configured to control an adhesive force with respect to the target object by adjusting an amount of air between the contact surface and the target object according to a detecting result of the sensor; and an actuator configured to control a movement of the ultrasound probe according to the detecting result of the sensor, wherein, the vacuum pump is configured to control the adhesive force to be smaller than a first reference value in response to the sensor detecting the user is touching said at least one of the ultrasound probe and the housing, the actuator is configured to move to be spaced apart from the ultrasound probe such that the ultrasound probe may move in response to the sensor not detecting the user is touching said at least one of the ultrasound probe and the housing, the vacuum pump is configured to control the adhesive force to be greater than the first reference value in response to the sensor not detecting the user is touching said at least one of the ultrasound probe and the housing, and the actuator is configured to move to contact the ultrasound probe such that the ultrasound probe is fixed in response to the sensor not detecting the user is touching said at least one of the ultrasound probe and the housing.

2. The support apparatus of claim 1, wherein the vacuum pump is configured to adjust an intensity of the adhesive force in steps.

3. The support apparatus of claim 1, wherein the actuator is configured to move the ultrasound probe in correspondence to a user command to move the ultrasound probe, in response to the user command being input through a communicator and the sensor not detecting the user is touching said at least one of the ultrasound probe and the housing.

4. The support apparatus of claim 3, wherein the actuator is configured to move the ultrasound probe according to a trace of a protocol in correspondence to the user command.

5. The support apparatus of claim 1, wherein the sensor comprises at least one of a touch sensor, a temperature sensor, a button sensor, a light sensor, and a pressure sensor.

6. A handsfree ultrasound apparatus comprising:

an ultrasound probe configured to irradiate ultrasound to a target object and receive an echo signal of the ultrasound;

a housing defining a space accommodating the ultrasound probe;

a contact surface for contacting the target object;

a sensor configured to detect whether a user touches the ultrasound probe;

a vacuum pump configured to control an adhesive force with respect to the target object according to a detecting result of the sensor; and an actuator configured to control a movement of the ultrasound probe according to the detecting result of the sensor, wherein, the vacuum pump is configured to control the adhesive force to be smaller than a first reference value in response to the sensor detecting the user is touching the ultrasound probe, the actuator is configured to be move to be spaced apart from the ultrasound probe such that the ultrasound probe may move in response to the sensor detecting the user is touching the ultrasound probe, the vacuum pump is configured to control the adhesive force to be greater than the first reference value in response to the sensor not detecting the user is touching the ultrasound probe, and the actuator is configured to move to contact the ultrasound probe such that the ultrasound probe is fixed in response to the sensor not detecting the user is touching the ultrasound probe.

7. A method of operating a handsfree ultrasound probe, the method comprising:

detecting, by a sensor, whether a user touches the handsfree ultrasound probe;

controlling, by a vacuum pump, an adhesive force adhering the handsfree ultrasound probe to a target object to be smaller than a first reference value when the sensor detects that the user touches the handsfree ultrasound probe;

controlling, by the vacuum pump, the adhesive force to be greater than the first reference value when the sensor does not detect that the user touches the handsfree ultrasound probe;

controlling, by an actuator, the handsfree probe such that the handsfree ultrasound probe may move by arranging the actuator to be spaced apart from the handsfree ultrasound probe when the sensor detects that the user touches the handsfree ultrasound probe; and controlling, by the actuator, the handsfree ultrasound probe to be fixed by the actuator contacting the handsfree ultrasound probe when the sensor does not detect that the user touches the handsfree ultrasound probe.

* * * * *